United States Patent [19]

Redmore

[11] 4,187,378

[45] Feb. 5, 1980

[54] PREPARATION OF PYRIDYL-4-PHOSPHONATES

[75] Inventor: Derek Redmore, Ballwin, Mo.

[73] Assignee: Petrolite Corporation, St. Louis, Mo.

[21] Appl. No.: 640,537

[22] Filed: Dec. 15, 1975

[51] Int. Cl.$^2$ .................................. C07D 213/04
[52] U.S. Cl. ........................................... 546/21
[58] Field of Search ................. 260/297 P; 546/21

[56] References Cited

U.S. PATENT DOCUMENTS

| | | | |
|---|---|---|---|
| 3,673,196 | 6/1972 | Redmore | 260/294.9 |
| 3,766,197 | 10/1973 | Redmore | 260/297 P |
| 3,770,750 | 11/1973 | Redmore | 260/294.8 R |
| 3,809,694 | 5/1974 | Redmore | 260/286 A |
| 3,810,907 | 5/1974 | Redmore | 260/297 P |

OTHER PUBLICATIONS

Nour et al., J. Chem. Soc. 1969, part C, pp. 2511 to 2513.
Okamoto et al., J. Org. Chem., vol. 35, pp. 3752 to 3755 (1970).

*Primary Examiner*—Alan L. Rotman
*Assistant Examiner*—Richard A. Schwartz
*Attorney, Agent, or Firm*—Sidney B. Ring; Hyman F. Glass

[57] ABSTRACT

This invention relates to the preparation of pyridyl-4-phosphonates by reacting phosphite ester salts with pyridines which are N-substituted with sterically hindering or "bulky" groups such as "bulky" phenyl groups, for example trityl, $\phi_3$C-.

9 Claims, No Drawings

PREPARATION OF PYRIDYL-4-PHOSPHONATES

In U.S. Pat. No. 3,673,196 there is disclosed and claimed a method of preparing predominantly 2-substituted nitrogen heterocyclics as illustrated by pyridines by reacting pyridines having a -NOR substitution with a salt of a phosphite ester as illustrated by the following equation

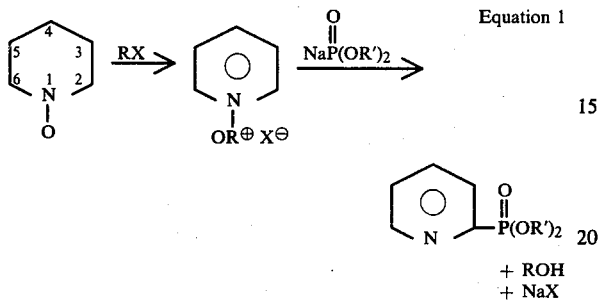

Equation 1

+ ROH
+ NaX

In equation 1, substitution in other than the 2-position may occur in the nature of a side reaction or where the 2-position is blocked.

I have now discovered a method of directing the substitution in the above equation to the 4-position instead of the 2-position by having the N-substitution a sterically hindering or "bulky" group such as "bulky" aromatic-containing groups, such as phenyl groups, for example the trityl group, $\phi_3 C$, etc., which are sufficiently bulky to prevent substitution in the 2-position of the pyridine ring.

This novel reaction is summarized in the following equation

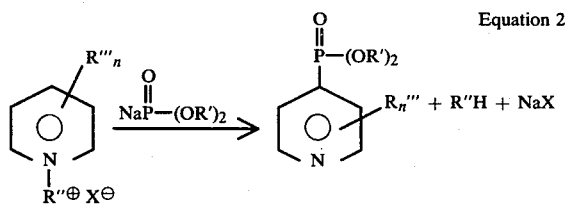

Equation 2 where R" is the sterically hindering or "bulky" group and R'" is a non-interfering group substituted on the pyridine ring, i.e., a group that does not interfere with substitution of

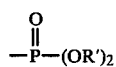

in the 4-position.

The reaction is most readily applicable to pyridine and 3 and/or 5 substituted pyridines. It can be applied to some 2-substituted pyridines but it is often difficult to prepare the N-trityl or other bulky salts thereof.

The key element in this procedure is the choice of N-substituent R". This group must be bulky so that it effectively prevents approach of the phosphorous nucleophile at the 2-position and as a result is forced to attack the 4-position. The ideal choice for R" is triphenylmethyl although other bulky groups such as fluorenyl,

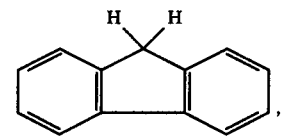

diphenylmethyl or other bulky group can be employed.

Any reactive salt of di-substituted phosphites can be employed

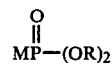

where M is a reactive metal and R is an ester moiety, preferably hydrocarbon or substituted hydrocarbon. Although alkali metal derivatives of diesters such as dialkyl phosphites are preferred, trialkyl phosphites can also be used. The preferred alkali metal derivatives of dialkyl phosphites are sodium or lithium derivatives of diethyl phosphite, diisopropyl phosphite, dipropyl phosphite, dibutyl phosphite, diphenyl phosphite, dibenzyl phosphite, etc.

The reaction sequence in detail is as follows:

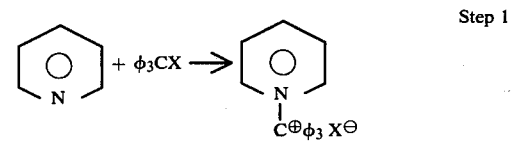

Step 1

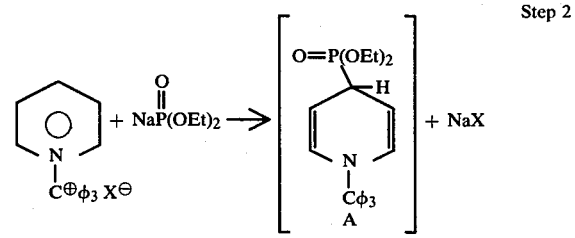

Step 2

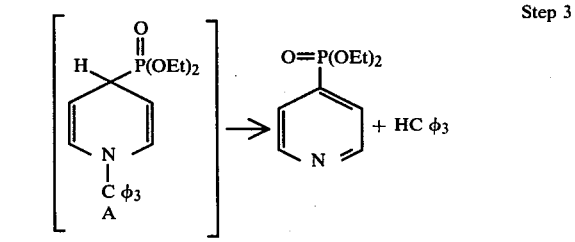

Step 3

A is not isolated but normally decomposes under the reaction conditions to the pyridyl-4-phosphonate.

X in the above can be any anion, for example, $-SO_4R$, $-SO_3R$, where R is alkyl, alkylphenol, etc., halogen such as chlorine, etc., but preferably Br, and most preferably $BF_4$, $ClO_4$, etc.

These compounds of this invention are readily hydrolyzed to the corresponding acids as illustrated by the following equation:

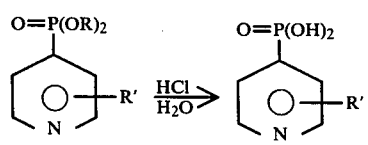

They can also be alkylated, etc.

The ester products of this invention are useful as corrosion inhibitors, biocides, etc. The acid products are useful chelating agents as scale, corrosion inhibitors, etc.

In general, the reaction is carried out in an inert solvent such as a hydrocarbon solvent, dipolar aprotic solvents such as dimethyl formamide, etc., ethers or mixtures thereof, which is water free at a temperature and time sufficient to promote the desired reaction. Temperature and time are interrelated. Thus a temperature of from 30° C. to the decomposition temperature of reactants and products can be employed. The upper limit of temperature being about 150° C. for 0.5-10 hrs., but preferably at reflux for about 1-3 hrs. The inorganic salt is separated from the organic layer by filtration or by water extraction and the phosphonate derivative is separated from the organic layer. In addition, the reaction is preferably carried out in an inert atmosphere such as nitrogen, argon, etc. In this way the attack of oxygen on the phosphite salts and the products is prevented.

The following examples are presented for purposes of illustration and not of limitation.

EXAMPLE 1

Diisopropyl pyridyl-4-phosphonate

Pyridine (10 ml) was added to a solution of triphenylcarbenium tetrafluoroborate (19 g; 0.058 mole) in methylene chloride (250 ml) with cooling. After standing at 5° overnight the resulting crystals, triphenylmethylpyridinium tetrafluoroborate 13.6 g were filtered. To a suspension of these crystals in benzene (130 ml) was added a solution of sodio diisopropylphosphite (0.035 mole) in diisopropyl phosphite (14 ml) during 45 minutes at 5°-10°. The mixture was heated at reflux for 2 hours, allowed to cool and water (50 ml) added. The organic phase was separated and extracted with 3 N HCl to recover the basic portion. Distillation of the crude base yielded pyridine and diisopropyl pyridyl-4-phosphonate 2.5 g (30%), bp 104°-5°/0.4 mm; nmr (CDCl$_3$) δ1.27(d,3H,J=6.5 Hz), 1.39 (d,3H,J=6.5 Hz), 4.78(m,2H) 7.65(m,2H), 8.75(m,2H).

EXAMPLE 2

Diethyl pyridyl-4-phosphonate

Using the method described in Example 1, treatment of trityl tetrafluoroborate with sodio diethylphosphonate yielded diethyl pyridyl-4-phosphonate
(39%), bp 101°-3°/0.5 mm. $^{31}$Pnmr−14.96 ppm.

Anal. Calcd. for C$_9$H$_{14}$NO$_3$P; C,50.23; H, 6.51; N,6.51;
P, 14.42.

Found, C,48.51; H,6.68; N, 6.12.

Warming the above ester in ethanol with picric acid gave a crystalline picrate. Recrystallization from ethanol gave the picrate, mp 152°-3°.

EXAMPLE 3

Diisopropyl 3-methylpyridyl-4-phosphonate

Crude triphenylmethyl-β-picolinium tetrafluoroborate from trityl tetrafluoroborate (50 g; 0.15 mole) and β-picoline (30 ml) in methylene chloride (400 ml) was isolated by evaporation of the solvent and dispersed in benzene (350 ml). Sodio diisopropyl phosphonate (0.15 mole) in diisopropyl phosphonate (40 ml) was added in 30 minutes at 5°-10°. After heating at reflux for 2 hours the reaction mixture was worked up in the manner described for Example 1. Distillation yielded excess β-picoline and diisopropyl 3-methylpyridyl-4-phosphonate, 20.6 g (53%), bp 103°-5°/0.1 mm; nmr δ (CDCl$_3$), 1.25 (d,J=6Hz), 2.57 (d, J=1.5 Hz), 4.75 (m, (7.79 H at C$_5$), 8.60 (m), $^{31}$P−12.9 ppm.

Anal. Calcd. for C$_{12}$H$_{20}$NO$_3$P: C, 56.03; H, 7.78; N, 5.45; P, 12.06.

Found: C, 54,35; H, 7.83; N, 5.18; P, 12.09.

Warming with picric acid in ethanol yielded a crystalline picrate which was recrystallized from ethanol to yield an analytical pure salt, mp 72°-4°.

EXAMPLE 4

Diisopropyl 3,5-dimethylpyridyl-4-phosphonate

The method used in Example 3 gave diisopropyl 3,5-dimethyl-pyridyl-4-phosphonate, 28%, bp 97°-99°/0.1 mm; nmr δ (CDCl$_3$) 1.18 (d, 3H, J=6Hz), 2.56(d, 6H, J=1.5 Hz), 4.70 (m,H$_3$), 8.25 (d,2H,J=6 Hz), $^{31}$P−13.6 ppm.

Anal. Calcd. for C$_{13}$H$_{22}$NO$_3$P; C, 57.56; H, 8.12; N, 5.17;
P, 11.44.

Found: C, 56.45; H, 8.24; N, 5.10; P, 11.15.

Warming in ethanol with picric acid yielded a picrate purified by recrystallization from ethanol, mp 139°-40°.

EXAMPLE 5

Pyridyl-4-phosphonic acid

The ester of Example 1 (2.5 g) was heated at reflux with 18% HCl (30 ml) for 4 hours. The gum obtained by evaporation of the aqueous acid yielded white crystals upon treatment with ethanol. Recrystallization from water/ethanol gave pure pyridyl-4-phosphonic acid 1.2 g (75%) mp > 300°.

Anal. Calcd. for C$_5$H$_6$NO$_3$P: C, 37.74; H, 3.77; N, 8.80;
P, 19.50.

Found C, 37.86; H, 4.00; N, 8.47; P, 19.83.

EXAMPLE 6

3-Methylpyridyl-4-phosphonic acid

Hydrolysis of the ester of Example 3 with 18% HCl yielded after crystallization from water/ethanol 3-methylpyridyl-4-phosphonic acid mp>300° in 95% yield.

Anal. Calcd. for C$_6$H$_8$NO$_3$P; C, 41.62; H, 4.62; N, 8.09;
P, 17.92.

Found: C, 41.85; H, 4.60; N, 7.85; P, 17.69.

EXAMPLE 7

3,5-Dimethylpyridyl-4-phosphonic acid

Hydrolysis of the ester of Example 4 in the normal manner gave after crystallization from water/ethanol the phosphonic acid, mp>300°, in 70% yield.

Anal. Calcd. for C$_7$H$_{10}$NO$_3$ P: C, 44.92; H, 5.35; N, 7.49;
P, 16.58.

Found: C, 44.89; H, 5.43; N, 7.46; P, 16.81.

I claim:

1. A process of preparing a pyridyl-4-dihydrocarbon phosphonate unsubstituted in a 2-position which comprises reacting in an inert solvent a phosphite compound (A) which is a metallic salt of a phosphite dihydrocarbon diester or is a trialkyl phosphite with compound (B)

which is an aromatic hydrocarbon N-substituted pyridinium salt unsubstituted in the 4-position and at least one of the two 2-positions, the said pyridinium salt being sterically hindered for reaction at a 2-position with said compound (A) by a sterically hindering bulky N-substituent which is a sufficiently bulky group to prevent substitution in the 2-position of the pyridine ring of compound (B).

2. A process for preparing a pyridyl-4-dihydrocarbon phosphonate unsubstituted in a 2-position which comprises reacting in an inert solvent a phosphite compound (A) which is an alkali metal salt of a phosphite dihydrocarbon diester or is a tri-lower alkyl phosphite with a compound (B) which is an aromatic hydrocarbon N-substituted pyridinium salt unsubstituted in the 4-position of the pyridine ring and at least one of the two 2-positions, the said pyridinium salt being sterically hindered for reaction at a 2-position with said compound (A) by a sterically hindering bulky N-substituent which is a sufficiently bulky group to prevent substitution in the 2-position of the pyridine ring of compound (B) and which is trityl, fluorenyl, or diphenyl methyl, the hydrocarbon groups of the phosphite diester being lower alkyl, phenyl, or benzyl.

3. The process of claim 1 wherein the phosphite is a salt of a phosphite dihydrocarbon diester.

4. The process of claim 2 where the phosphite is the alkali metal dihydrocarbon phosphite diester.

5. The process of claim 4 where the alkali metal phosphite diester is sodium dialkyl phosphite.

6. The process of claim 5 where the bulky group is trityl.

7. The process of claim 4 where the reaction is carried out at a temperature of from 30° C. to the decomposition temperature of the reactants and products and in an inert atmosphere, the inert solvent being organic solvent which forms a separate phase when water is added, adding water to the reaction products, and recovering the desired pyridyl-4-dihydrocarbon phosphonate unsubstituted in a 2-position from the organic solvent phase.

8. The process of claim 7 where the pyridine ring is methyl substituted and the dihydrocarbon groups of the phosphite are isopropyl groups.

9. The process which comprises admixing triphenylmethylpyridinium tetrafluoroborate in benzene with sodio diisopropyl phosphite in diisopropyl phosphite, refluxing the mixture, cooling, adding water and recovering diisopropyl pyridyl-4-phosphonate from the separated organic phase.

* * * * *